Figure 1:
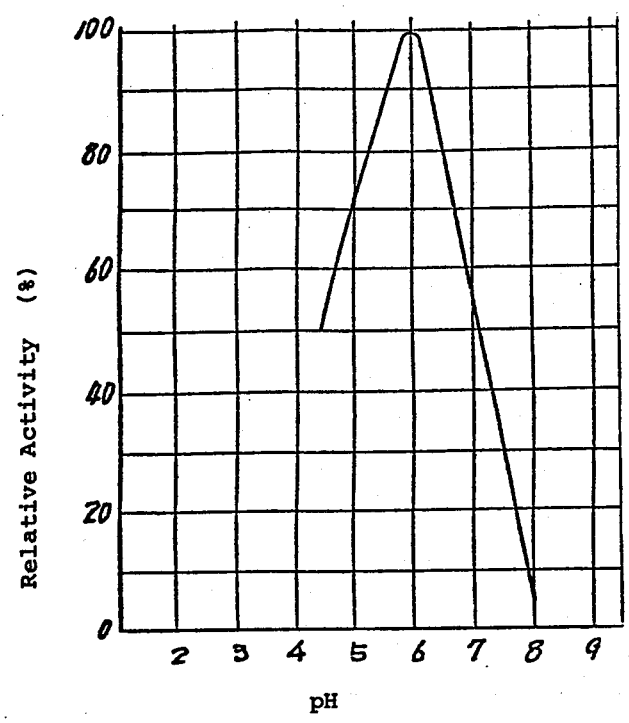
Figure 2:
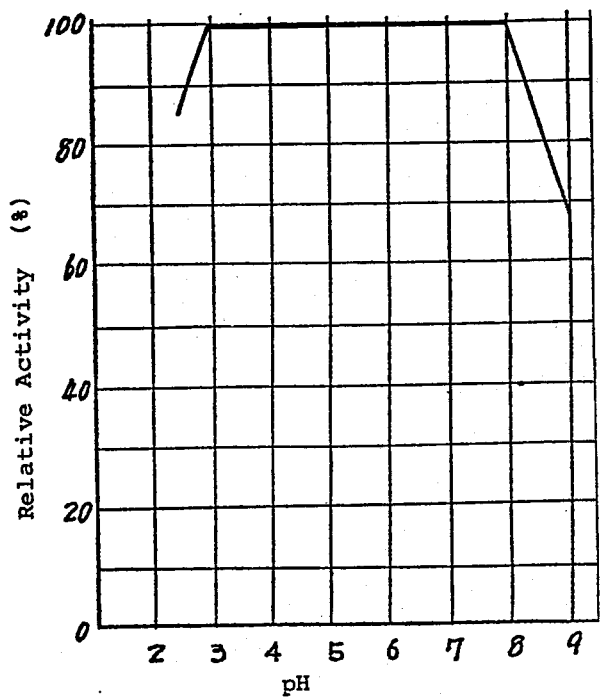
Figure 3:
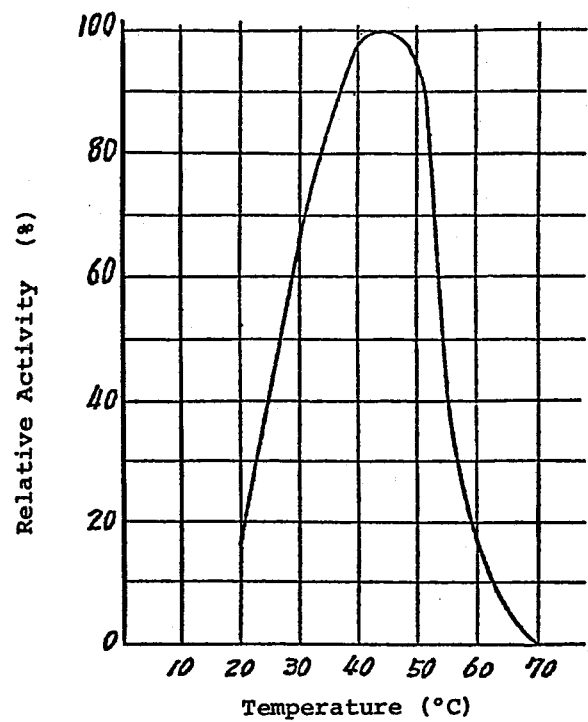
Figure 4:
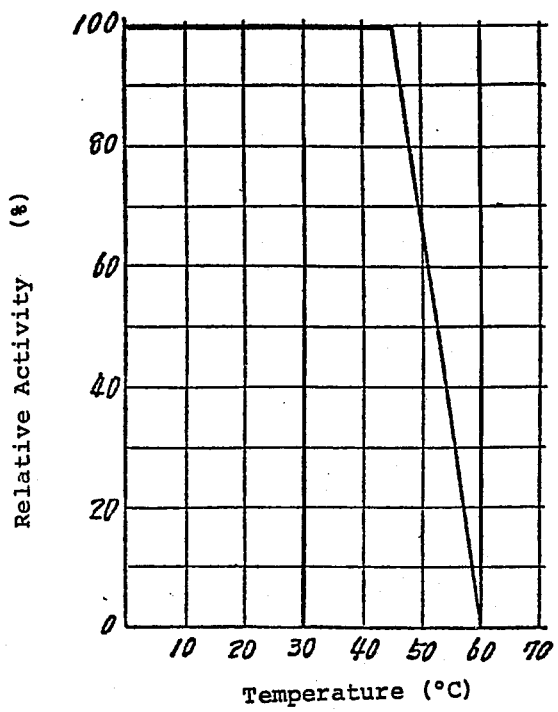

United States Patent [19]

Yokobayashi et al.

[11] 4,072,567
[45] Feb. 7, 1978

[54] COMPOUND WATER-INSOLUBLE GLUCAN AND PROCESS FOR THE PRODUCTION THEREOF

[75] Inventors: Koji Yokobayashi, Okayama; Tadashi Ikeda, Tokyo; Akira Misaki, Hyoogo, all of Japan

[73] Assignee: Kabushiki Kaisha Hayashibara Seibutsu Kagaku Kenkyujo, Okayama, Japan

[21] Appl. No.: 749,520

[22] Filed: Dec. 10, 1976

[30] Foreign Application Priority Data

Dec. 11, 1975 Japan .............................. 50-147854

[51] Int. Cl.$^2$ ...................... C12D 13/04; C07G 3/00; C08B 37/00
[52] U.S. Cl. ................................... 195/63; 195/31 P; 195/96; 536/1
[58] Field of Search .................... 195/31 P, 96, 63, 68; 536/1, 4

[56] References Cited

PUBLICATIONS

Ebisu et al., "Studies on the Structures of Polysaccharides (Glucans and Fractans) Produced by Cariogenic Streptococci and on an Enzyme Hydrolyzing the Insoluble Glucan. I. Structural Studies of Insoluble Glucan, Soluble Glucan, and Fractans." *Chemical Abstracts*, vol. 85, No. 21, pp. 235, 236 (1976), Abs. No. 156181a.

Ebisu et al., "The Structure of Water-Insoluble Glucans of Cariogenic Streptococcus Mutans, Formed in the Absence and Presence of Dextranase," *Carbohydrate Research*, vol. 38 (1974), pp. 374-381.

Baird et al., "Investigation of the Polysaccharides Produced by Extracellular Glycosyltransferases from Streptococcus Mutans," *Chemical Abstracts*, vol. 77, No. 11, p. 242 (1972), Abs. No. 72399z.

Jeanes et al., "Characterization and Classification of Dextrans from Ninety-Six Strains of Bacteria," *J. Amer. Chem. Soc.*, vol. 76, No. 20, (1954), pp. 5041-5042.

Primary Examiner—Raymond N. Jones
Assistant Examiner—Thomas G. Wiseman
Attorney, Agent, or Firm—Browdy and Neimark

[57] ABSTRACT

A culture medium composed of carbon source, nitrogen source and minerals was sterilized at 120° for 15 minutes, inoculated with strains of the genus Streptococcus and then cultivated at 35° C for 72 hours under aeration and agitation. Subsequent to the cultivation, the resultant was subjected to water-washing and sieving to obtain crude glucan. The crude glucan was then dissolved in NaOH solution and centrifuged. The recovered filtrate was neutralized with HCl and then the insolubilized glucan was collected by centrifugation. The collected glucan was washed with water thoroughly until no chloride ion was detected in the waste water and then dried to form white purified glucan powder.

3 Claims, 5 Drawing Figures

COMPOUND WATER-INSOLUBLE GLUCAN AND PROCESS FOR THE PRODUCTION THEREOF

The present invention relates to a novel water-insoluble glucan comprising alpha-(1→3), (1→4) and (1→6) glucosidic linkages and processes for the production thereof.

Polysaccharides have been used extensively in the food, cosmetic, pharmaceutical, paper manufacturing and chemical industries, and the consumption is showing a yearly increase. Although higher plants and sea weeds had served as the major sources of polysaccharides, microbial polysaccharides which are suppliable stably and at all times, were developed recently and have become commercially available. Most of the microbial polysaccharides developed so far are, however, water soluble and viscous.

The present inventors, envisaging the production and potential uses of water-insoluble glucan, devoted themselves to the necessary studies which resulted in the discovery that a so-far-unknown highly-branched, water-insoluble glucan comprising alpha-(1→3), (1→4) and (1→6) glucosidic linkages (hereinafter referred to as the water-insoluble glucan) is producible in high yield.

The water-insoluble glucan according to the present invention is obtained in forms such as pellicles, particles, beads and pellets, and unlike viscous, water-soluble glucans, no highly inflammable or explosive precipitants, such as methanol, ethanol and acetones are required in their production. Moreover, since the culture broth of the water-insoluble glucan and the water-insoluble glucan hardly exhibit viscosity or tackiness, the formed water-insoluble glucan is separable and recoverable from the culture broth with extreme ease by using such simple means as natural sedimentation, filtration or sieving. Accordingly, the present invention provides production of a water-insoluble glucan wherein a drastic reduction in production time, in comparison with that for water-soluble glucans, is realizable.

In addition, the inventors found that additional fresh water-insoluble glucan is obtainable by simply allowing the crude water-insoluble glucan, prepared and which has a water-insoluble glucan-producing activity according to the present invention, to contact with an aqueous sucrose solution and thereby effecting a reaction therebetween, as well as that such water-insoluble glucan-producing activity is stable over long periods. Presumably, this suggests that a glucan-producing enzyme or a cell containing such enzyme is present in an immobilized form in the crude glucan obtained by the cultivation.

Since the possibility of the occurrence of contamination by nutrient medium is lower than in the cases of cultivation, the water-insoluble glucan produced by allowing the crude glucan to contact with an aqueous sucrose solution to effect reaction possesses a higher purity.

The crude glucan thus obtained can be purified by dissolving the crude product in, for example, 0.5–1.0N aqueous alkali metal hydroxide solution, centrifuging the resulting solution, and then neutralizing the supernatant thereof. The purification will provide a water-insoluble glucan product. Repetition of the procedures and thorough water-washing yield the purified water-insoluble glucan of the present invention.

The present invention will be illustrated in further detail.

Any bacterium of genus *Streptococcus* which is capable of producing the water-insoluble glucan from sucrose as specified is employable. One example of an employable bacteria which possesses a high glucan-producing activity and gives favorable results is *Streptococcus salivarius* TTL-LP$_1$ FERM-P No. 3310, derived from the saliva of healthy persons. Identification of the strain was carried out by collating its morphological and physiological characteristics with those described in *Bergey's Mannual of Determinative Bacteriology*, 8th edition (1974). The results of collation were as follows.

The morphological and physiological characteristics of *Streptococcus* sp. TTL-LP$_1$ Cells spherical to ovoid with 0.8–1.0 microns in diameter, occurring in pairs or chains of varing length from short to long when grown in liquid media. Non-motile. Endospores not formed. Gram-positive. Not acid-fast.

Agar colonies: Round, smooth, entire to undulate, convex, creamy white, opaque. Punctiform on bouillon agar. About 0.8–1.2 mm in diameter on glucose bouillon agar.

Agar slant: Moist and glistening, slightly raised, creamy white to grayish white, spreading. Growth thin and late on bouillon agar. Growth moderate on glucose bouillon agar.

Broth: Turbid; clear with creamy white to grayish white sediment easily dispersed. No pellicle. Growth weak with light sediment in bouillon. Growth abundant with sediment in glucose bouillon. Final pH range in glucose bouillon broth is 3.8–4.2.

Gelatin stab: No liquefaction. Filiform growth.

Colonies on 5% sucrose and raffinose agar: Produces large mucoid colonies with white, translucent, round, entire, glistening and capitate appearance on raffinose agar, whereas does mucoid colonies with white, translucent, round, entire, smooth, glistening and capitate appearance, becoming large pyramid or conical form colonies with white, translucent, rough, moist and glistening, undulate or angular and cheese-like appearance in old cultures on sucrose agar.

Litmus milk: Acid, coagulated; not peptonized. Reduces litmus only in the bottom of tube without reducing before curdling milk and then oxidizes.

Nitrites not produced from nitrates.

No denitrification.

Methyl red test positive.

Voges-Proskauer test negative.

Indole not produced.

Hydrogen sulfide not produced.

Starch not hydrolyzed.

Citrates not utilized (Koser's and Christensen's citrate media).

Utilizes nitrates, but does not ammonium salts as sole source of nitrogen.

Pigments not formed.

Urea not attacked.

Oxidase not produced.

Catalase not produced.

Acid and gas from carbohydrates: Acid but no gas from glucose, fructose, galactose, sucrose, maltose, lactose, raffinose, trehalose, inulin, inositol and salicin. No acid and gas from glycerol, sorbitol, mannitol, xylose, arabinose and starch.

Predominant end product of glucose fermentation is dextrorotatory lactic acid.

Esculin hydrolyzed.

Hippurates not hydrolyzed.

Does not produce ammonia from arginine.

Beta-hemolytic.

Heat tolerance: Does not survive 60° C for 30 minutes.

NaCl tolerance: Grows in 2% NaCl broth, but does not in 6.5% NaCl broth.

Methylene blue tolerance: Does not grow in 0.1% methylene blue milk.

Bile tolerance: Does not grow on 40% bile blood agar.

Bile solubility negative.

Benzidine test negative.

Growth pH: Optimum, about 7. Grows at pH 5.5–8.0. Does not grow at pH 9.6.

Growth temperature: Optimum, 37° C. Grows at 20°–45° C. Does not grow at 10° or 47° C.

Facultatively anaerobic.

Collation of the following morphological and physiological characteristics with those described in *Bergey's Mannual of Determinative Bacteriology*, 8th edition (1974) showed that the strain is bacterium of genus *Streptococcus*. Chemoorganotrophic; cells do not glide; products of binary fission are equivalent; cells rigidly bound; endospores not formed; gram-positive; do not contain hemocompounds; catalase negative; metabolism of carbohydrates fermentative; predominant end product of glucose fermentation is dextrorotatory lactic acid; and cocci. Furthermore, the following physiological characteristics show that the strain is that of *Streptococcus salivarius*.

Growth pH, growth temperature; heat tolerance; oxygen demand; NaCl, methylene blue and bile tolerances; bile solubility; hemolysis; hydrolysis of arginine, starch, gelatin, hippurate and esculin; and fermentation of carbohydrates. Based on these observations, the strain was designated as *Streptococcus salivarius* TTL-LP$_1$ and deposited to the Fermentation Institute, Agency of Industrial Science and Technology, 8-1, 5-Chome, Inagehigashi, Chiba, Japan, which assigned it the FERM-P No. of 3310.

In the invention, the bacterium of genus *Streptococcus*, wherein the aforementioned strain is present, is cultivated on a medium containing sucrose as the major carbon source, nitrogen source, minerals and other nutrients necessary for the cell growth. Although the culture medium may be in solid or liquid form, a liquid medium is generally used. The water-insoluble glucan of the invention may be produced by static culture, but shaking culture or aeration-agitation culture results in higher glucan yield, up to 30–45% against material sucrose, w/w, dry solid basis (hereinafter referred to as d.s.b.).

Sucrose is most suitable as carbon source in the invention and the desirable concentration range is 1–30%, w/v. Synthetic compounds, such as nitrates, ammonium salts, urea and natural organic substances such as polypeptone, corn steep liquor, yeast extract and amino acids may be used freely as nitrogen source. If necessary, inorganic salts such as phosphates, sulfates, potassium salts, calcium salts, magnesium salts, manganese salts and ferrate are employable. Vitamins, nucleic acids and their analogs may be also added to the culture medium as growth factors. The initial pH, when the microorganism starts growing and producing the water-insoluble glucan, is generally in the range of 6.0–8.0. The cultivation is carried out until maximum glucan production is attained, which usually requires 24 to 96 hours. The inventors discovered that the water-insoluble glucan, which accumulates in the culture medium, possesses the activity of producing glucan from sucrose, and studied various means to isolate the glucan-producing substance, but without success. The reason that the isolation attempts resulted unsuccessful may be due to the fact that the glucan-producing activity present in the crude glucan are attributed to the possible immobilization of glucan-producing enzyme or cells containing the enzyme on the glucan.

The glucan-producing activity was determined as follows. The amount of fructose liberated by reacting a mixture, prepared by adding 0.5 ml of an aqueous suspension of ground crude glucan to 10 ml of a 0.05M phosphate buffer solution pH 6.5 containing 5% sucrose at a temperature of 40° C for 15 minutes, was measured and the activity that liberates one $\mu$ mol of fructose per minute at a temperature of 40° C was designated as one unit. The glucan-producing activity of the crude glucan obtained by cultivation according to the invention is about 0.5–50 units/gram, wet solid basis.

Figure 5:
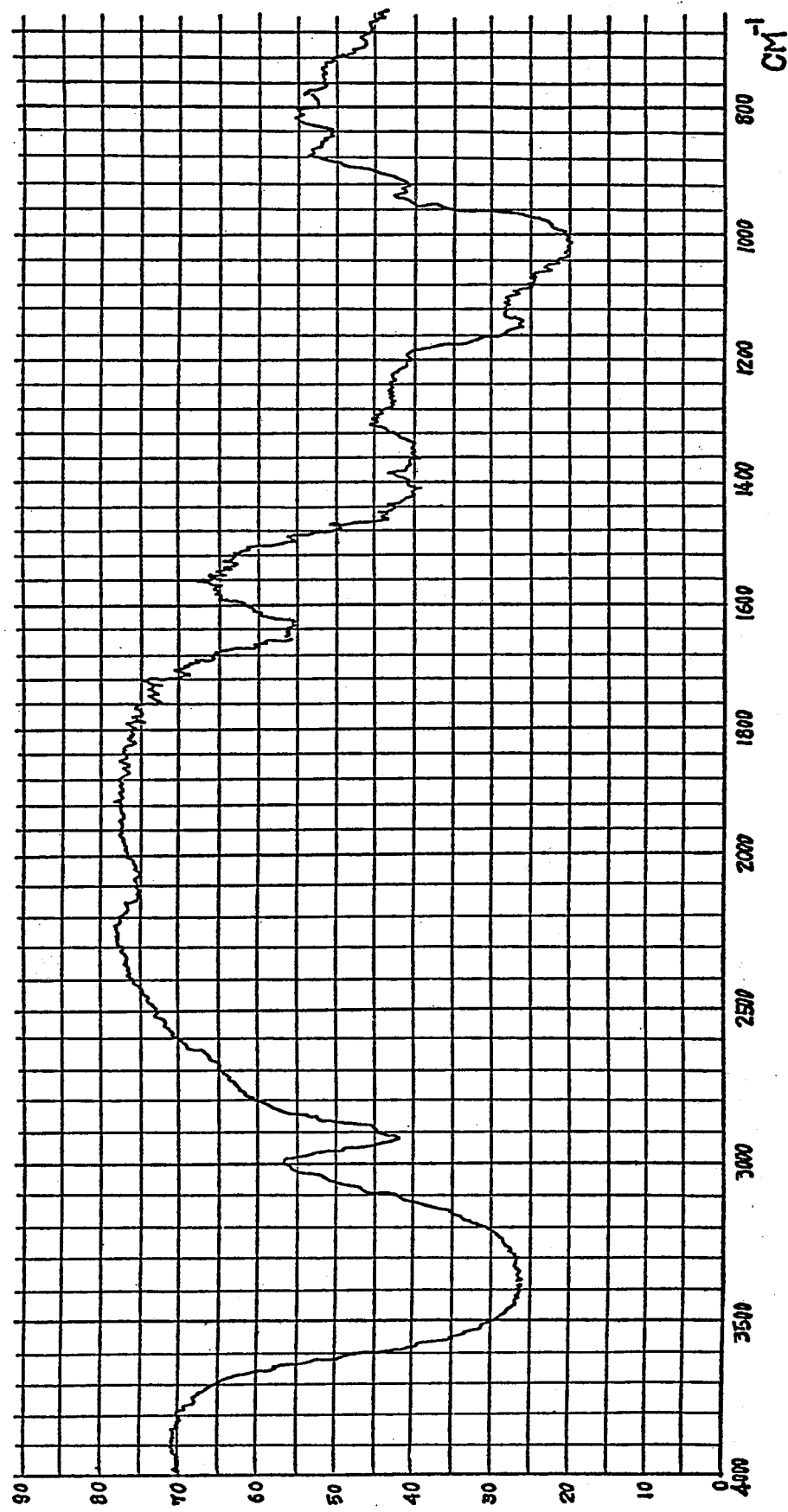

FIGS. 1–4 show the properties of the glucan-producing activity. More particularly, FIGS. 1,2,3 and 4, respectively, show the optimum pH, pH stability, optimum temperature and heat stability. In FIG. 5 is shown the infrared spectrum of the purified water-insoluble glucan.

The substrate specificity of the glucan-producing activity was investigated with sucrose, maltose, trehalose, isomaltose, maltitol, lactitol, cellobiose, maltulose, turanose, melezitose and melibiose, and the formed fructose or glucose was determined. The results showed that the activity is only specific on sucrose and trehalose and that sucrose is about 50 times susceptive than trehalose. Water-insoluble glucan can be produced with the crude glucan possessing the glucan-produding activity by allowing the crude glucan to contact with an aqueous sucrose solution and thereby effecting reaction therebetween. The process can be carried out by either the batch system wherein the crude glucan are added to an aqueous sucrose solution and effecting reaction of the mixture under occasional agitation, or by a continuous system wherein the crude glucan is packed in a column and allowing an aqueous sucrose solution to pass therethrough. As to reaction conditions, a sucrose concentration in the range of 1–30%, w/v, a pH value within the range of 5–7 and a temperature within the range of 35°–50° C are preferable. An employment of 0.1–10 units of glucan-producing activity per gram sucrose is more practical.

The water-insoluble glucan in accordance with the invention is produced during the above-described cultivation or reaction. Because the glucan thus produced or accumulated is insoluble in water and is non-tacky, the water-insoluble glucan can be separated and recovered from the culture broth or reaction mixture by using simple processes such as natural sedimentation, filtration or sieving. In addition, the water-washed product can be used as immobilized glucan-producing enzyme which is stable over prolonged storage.

White powder product is obtainable by drying the glucan intact or after purification. Since the product is water-insoluble, the characteristics of the product can be utilized for many applications. For example, the water-insoluble glucan can be used for preparing feeds for fish culture, which is difficultly water-soluble and which prevent contamination or pollution of the fish-breeding ponds.

If necessary, the water-insoluble glucan, similarly as in the cases of starch and cellulose, can be chemically modified into water-soluble glucans.

The purified glucan product obtained in accordance with the procedures described in Example 1, infra, was tested to prove that the water-insoluble glucan of the present invention is a so-far-unknown, new polysaccharide.

The results were as follows:

Purity: No contaminants are detectable on subjection to ultracentrifugation and electrophoresis.

Element analysis: C=40.71%, H=63.1%, N=0%

Ash: Not more than 0.01%

Specific rotation: $[\alpha]_D^{25}$ +225° (1=0.5, c=0.5, 1N-NaOH)

Solubility: Dissolves readily in 0.5N-NaOH, slightly in 90% formic acid and dimethyl sulfoxide and is insoluble in organic solvents such as methanol, acetone and chloroform.

Description: A tasteless, odorless, white fine powder.

Color reaction: Turns into green by the anthrone-sulfuric reaction, and into reddish brown by the indole-hydrogen chloride reaction. Iodine stain, negative.

Ultraviolet spectrum: Shows an absorption at a wavelength of 195 nm or shorter.

Infrared spectrum: Infrared spectrum by the KB$_r$ tablet method is as shown in FIG. 5.

Limiting viscosity number: $[\eta]=2.5$

Sedimentation constant: $S_{20W}=4.9$

Component: The Rf value of paperchromatography of sugar obtained by four-hour hydrolysis with 2N-hydrochloric acid, retention time of gas chramatogram and results of glucose oxidase and peroxidase tests show that the polysaccharide of the present invention contains glucose as its predominant component.

Linkage: Periodate oxidation or methylation, chemical analysis by the Smith degradation or controlled Smith degradation, and enzymatic analysis with isomaltodextranase give the following results:

From periodate oxidation, the formic acid formation is found as about 0.3 moles per mole glucose residue, and periodate consumption about 0.95 moles per mole glucose residue.

The decomposition products of the methylated glucan, i.e. 2,3,4,6-tetra-O-methyl-D-glucose, 2,4,6-tri-O-methyl-D-glucose, 2,3,4- and 2,3,6-tri-O-methyl-D-glucose, and 2,4-di-O-methyl-D-glucose, are determined quantatively by gas chromatography and mass spectrum, and the molar ratio of the compounds, and molar ratio of the glycerol and erithritol in Smith degradation and controlled Smith degradation are analysed qualitatively and quantitatively by paper- and gas-chromatographies. From the results, the linkage proportions of the glucose residues in the water-insoluble glucan are non-reducing terminal residues, 16.2%; alpha- (1→3)-linkage residues, 36.1%; alpha-(1→6)-linkage residues, 24.9%; alpha-(1→4)-linkage residues, 6.8%; and alpha-(1→3)- and alpha-(1→6)-branched linkages residues 16.0%.

From the fact that if the proportion of non-reducing terminal glucose residues is assigned 2 the above proportions will be approximately 4:3:1:2, the repeated unit of glucose residues in the water-insoluble glucan is assumable as being 12.

In addition, the fact that the isomaltodextranase, derived from a strain of genus *Arthrobacter* and which liberates isomaltose from the non-reducing terminals of dextran, form a small amount of isomaltose when allowed to act on the water-insoluble glucan indicates that the glucan contains isomaltose structure on its non-reducing terminals.

All-around studies of the results and those of the aforementioned specific rotation and infrared spectrum indicate that alpha-(1→3)-glucosidic linkages are predominatly present in the main chains of the water-insoluble glucan, that one of three glucose residues in the main chain has a branched chain, and that proportion of alpha-(1→4)-glucosidic linkages in the branched chains is about one-third of the alpha-(1→6)-glucosidic linkages.

In other words the glucan produced by the process of the present invention is a novel water-insoluble glucan with high degrees of branching and which is constructed by repeatedly linked units of 12 glucose residues that are mainly linked alpha-(1→3), (1→4) and (1→6).

The present invention will be described in further details with reference to examples.

EXAMPLE 1

A culture medium comprising polypeptone 0.6%, w/v, sodium acetate 1.0%, w/v, $K_2HPO_4$ 0.05%, w/v, $KH_2PO_4$ 0.05%, w/v, $NH_4Cl$ 0.3%, w/v, yeast extract 0.1%, w/v, $MgSO_4.7H_2O$ 0.5%, w/v, $MnSO_4. 4H_2O$ 0.04%, w/v, sucrose 7%, w/v and tap water was sterilized at 120° C for 15 minutes, inoculated with strains of *Streptococcus salivarius* TTL-LP$_1$ FERM-P No. 3310 and then cultivated at 35° C for 72 hours under aeration and agitation. Subsequent of the cultivation, the resultant was subjected to water-washing and sieving to obtain crude glucan at a yield of about 43%, d.s.b., against sucrose. The nitrogen and ash contents of the thus obtained crude glucan were respectively 0.25% and 0.17%. The crude glucan was then dissolved in a 1N-NaOH solution and centrifuged at 10,000G for 15 minutes. The recovered filtrate was neutralized with 0.5N–HCl and then the insolubilized glucan was collected by centrifugation. After repetition of the procedures four times, the collected glucan was washed with water thoroughly until no chloride ion was detected in the waste water and then dried to form white purified glucan powder at a yield of about 34%, w/w. d.s.b. against sucrose.

EXAMPLE 2

Wet crude glucan, obtained in accordance with the procedures described in Example 1 and which contains about 5 units of glucan-producing activity per gram wet glucan, in the amount of 500 grams was packed in a column and 12 ml of a 10% aqueous sucrose solution (pH 6.0) was allowed passage through the column at a temperature of 45° C and a space velocity of about one per hour.

Thereafter, the glucan in the column was washed thoroughly with water and the glucan yield against sucrose was determined about 30%, w/w, d.s.b. by investigating the increase in weight. The activity of the employed crude glucan showed no decrease by the reaction and was found reusable. Subsequent of purification according to the procedures, the glucan product showed similar physical and chemical properties as the water-insoluble glucan product of Example 1. Further, analysis of the sugar liquid which eluted from the column showed it was an intensively-sweet, and difficultlycrystallizable syrup containing high proportions of sucrose and fructose and a small amount of glucose. The yield of the syrup was about 70%, w/w, d.s.b., against sucrose.

What is claimed is:

1. A water-insoluble glucan composed of non-reducing terminal residues, alpha-(1→3)-linkage residues, alpha-(1→6)-linkage residues, alpha-(1→4)-linkage residues and alpha-(1→3)- and alpha-(1→6)-branched linkage residues in the ratio of 2:4:3:1:2.

2. A process for the production of a water-insoluble glucan including alpha-(1→3), (1→4) and (1→6) glucosidic linkages, comprising cultivating *Streptococcus salivarius* TTL-LP$_1$ FERM-P No. 3310 on a sucroce-containing medium to form the water-insoluble glucan, and separating and recovering the glucan from the resulting culture broth.

3. A process for the production of water-insoluble glucan including alpha(1→3), (1→4) and (1→6) glucosidic linkages, comprising cultivating *Streptocuccus salivarius* TTL-LP$_1$ FERM-P No. 3310 on a sucrose-containing medium to form the water-insoluble glucan, allowing the water-insoluble glucan to contact an aqueous sucrose solution to effect reaction of the mixture and to form more of the water-insoluble glucan, and separating and recovering the water-insoluble glucan from the reaction mixture.

* * * * *